United States Patent [19]

Li et al.

[11] Patent Number: 5,064,636

[45] Date of Patent: Nov. 12, 1991

[54] PARAMAGNETIC OIL EMULSIONS AS ENTERIC MRI CONTRAST AGENTS

[76] Inventors: King C. P. Li, 2839 NW. 35th Pl.; Peter G. P. Ang, 2932 NW. 24th Ter., both of Gainesville, Fla. 32605

[21] Appl. No.: 424,053

[22] Filed: Oct. 19, 1989

[51] Int. Cl.$^5$ .................... G01N 31/00; G01N 24/00; A61K 31/20; A61K 31/19

[52] U.S. Cl. ........................................ 424/9; 424/535; 436/173; 514/558; 514/560; 514/574; 514/943; 514/974; 514/975

[58] Field of Search ............... 514/574, 558, 560, 943, 514/974, 975; 424/9, 535; 436/173; 128/653, 653 AF, 653 CA, 654

[56] References Cited

U.S. PATENT DOCUMENTS

| | | | |
|---|---|---|---|
| 3,992,555 | 11/1976 | Kovacs | 426/72 |
| 4,216,236 | 8/1980 | Mueller et al. | 426/72 |
| 4,544,545 | 10/1985 | Ryan et al. | 424/1.1 |
| 4,615,879 | 10/1986 | Runge et al. | 424/9 |
| 4,675,173 | 6/1987 | Widder | 424/9 |
| 4,719,098 | 1/1988 | Weinmann et al. | 424/9 |
| 4,728,575 | 3/1988 | Gamble et al. | 428/402.2 |
| 4,731,239 | 3/1988 | Gordon | 424/9 |
| 4,827,945 | 5/1989 | Groman et al. | 128/653 R |
| 4,863,716 | 9/1989 | Quay et al. | 424/9 |

FOREIGN PATENT DOCUMENTS

0245019 11/1987 European Pat. Off. .

OTHER PUBLICATIONS

Clanton, Jeffrey, A., "Oral Contrast Agents", *Magnetic Resonance Imaging*, vol. I, Chap. 48, pp. 830-837, W. B. Saunders Company (1988).

Stark, David D. and Bradley, William G., Jr., "Gastrointenstinal Contrast Agents", *Magnetic Resonance Imaging*, pp. 1134-1139, The C. V. Mosby Company, St. Louis, MO (1988).

Burnett, K. R., Goldstein, E. J., Wolf, G. L., Sen. S., and Mamourian, A. C., "The Oral Administration of $MnCL_2$: A Potential Alternative to IV Injection for Tissue Contrast Enhancement in Magnetic Resonance Imaging", *Magnetic Resonance Imaging*, vol. 2, pp. 307-314, Pergamon Press, Ltd. (1984).

Mamourian, A. C., Burnett, K. R., Goldstein, E. J., Wolf, G. L., Kressel, H. Y. and Baum, S., "Proton Relaxation Enhancement in Tissue Due to Ingested Manganese Chloride: Time Course and Dose Response in the Rat", *Physiological Chemistry and Physics and Medical NMR*, 16, pp. 123-128 (1984).

Wesbey, G. E., Brasch, R. C., Goldberg, H. I., and Engelstad, B. L., "Dilute Oral Iron Solutions as Gastrointestinal Contrast Agents for Magnetic Resonance Imaging; Initial Clinical Experience", *Magnetic Resonance Imaging*, vol. 3, pp. 57-64 (1985).

Runge, V. M., Stewart, R. G., Clanton, J. A., Jones, M. M., Lukhart, C. M., Partain, C. L., and James, A. E.., Jr., "Work In Progress: Potential Oral and Intravenous Paramagnetic NMR Contrast Agents", *Radiology*, vol. 147, No. 3, pp. 789-791 (Jun. 1983).

Newhouse, J. H., Brady, T. J., Gebhardt, M., Burt, C. T., Pykett, I. L., Goldman, M. R., Buonanno, F. S., Kistler, J. P., Hinshaw, W. S., and Pohost, G. M., "NMR Imaging: Preliminary Results in the Upper Extremities of Man and the Abdomen of Small Animals", *Radiology*, vol. 142, No. 1, p. 246 (Jan. 1982).

Pauls T. Beall, "Safe Common Agents for Improved NMR Contrast", *Physiological Chemistry and Physics and Medical NMR*, No. 16, pp. 129-135 (1984).

Chen, B., Gore, J. C., Zhong, J. H., McCarthy, S., Lange R. C., Helzberg, J. Young, R. S. K., and Wong, M., "Gastrointestinal MRI Contrast Enhancement by Liquid Food", *Proceedings of the 7th Annual Meeting of the Society of Magnetic Resonance in Medicine*, pp. 733 (1988).

G. S. Bissett III, "Evaulation of Potential Practical Oral Contrast Agents for Pediatric Magnetic Resonance Imaging", *Pediatric Radiology*, 20:61-66 (1989).

Raptopoulos, V., Davis, M. A., Davidoff, A., Karellas, A., Hays, D., D'Orsi, C. J., and Smith, E. H., "Fat-Density Oral Contrast Agent for Abdominal CT," *Radiology*, 164:653-656 (1987).

Raptopoulos, V., Davis, M. A., and Smith, E. H., "Imaging of the Bowel Wall: Computed Tomography and Fat Density Oral-Contrast Agent in an Animal Model", *Radiology*, 21: 847-850 (1986).

Baldwin, G. N., "Computed Tomography of the Pancreas: Negative Contrast Medium", *Radiology*, 128:827-828 (1978).

Young, I. R., Clarke, G. J., Bailes, D. R., Pennock, J. M., Doyle, F. H., and Bydder, G. M., "Enhancement of Relaxation Rate with Paramagnetic Contrast Agents in NMR Imaging", *Computed Tomography*, vol. 5, No. 6, pp. 543-547 (1981).

Laniado, M., Kornmesser, W., Hamm, B., Clauss, W., Weinmann, H-J., and Felix, R., "MR Imaging of the Gastrointestinal Tract: Value of Gd-DTPA", *Amer. Journ. of Roentgenology*, 150:817-821 (Apr. 1988).

(List continued on next page.)

*Primary Examiner*—Glennon H. Hollrah
*Assistant Examiner*—Gary Hollinden
*Attorney, Agent, or Firm*—Thomas W. Speckman; Douglas H. Pauley

[57] ABSTRACT

A paramagnetic oil emulsion for enteric administration composed of about 5 to about 30 volume percent oil and about 70 to about 95 volume percent aqueous-based paramagnetic carrier, the aqueous-based paramagnetic carrier having a magnetic resonance contrast effective and less than a toxic amount of at least one water-soluble paramagnetic agent. The paramagetic oil emulsion provides high intensity magnetic resonance signals in the gastro-intestinal tract for MRI evaluation of the abdomen and pelvis.

35 Claims, No Drawings

OTHER PUBLICATIONS

Widder, D. J., Edelman, R. R., Grief, W. L. and Monda, L., "Magnetite Albumin Suspension: A Superparamagnetic Oral MR Contrast Agent", *Amer. Journ. of Roentgenology*, 149:838-843 (Oct. 1987).

Hahn, P. F., Stark, D. D., Saini, S., Lewis, J. M., Wittenberg, J., and Ferrucci, J. T., "Ferrite Particles for Bowel Contrast in MR Imaging: Design Issues and Feasibility Studies", *Radiology*, 164, pp. 37-41 (Jul., 1987).

Li, K. C. P., Tart, R. P., Storm, B., Rolfes, R., Ang, P., and Ros, P. R., "MRI Oral Contrast Agents: Comparative Study of Five Potential Agents in Humans", Proceedings of the Eighth Annual Meeting of the Society of Magnetic Resonance in Medicine, Amsterdam, Aug. 18, 1989, p. 791.

Weinreb, J. C., Maravilla, K. R., Redman, H. C., and Nunnally, R., "Improved MR Imaging of the Upper Abdomen with Glucagon and Gas", *J. Comput. Assist. Tomogr.*, vol. 8, pp. 835-838 (1984).

Mattrey, R. F., Hajek, P. C., Gylys-Morin, V. M., Baker, L. L., Martin, J., Long, D. C., and Long, D. M., "Perfluorochemicals as Gastrointenstinal Contrast Agents for MR Imaging: Premliminary Studes in Rats and Humans", *Amer. Jour. of Roentgenology*, 148, pp. 1259-1263 (Jun. 1987).

Mattrey, R. F., "Perfluorooctylbromide: A New Contrast Agent for CT, Sonography, and MR Imaging", *Amer. Jour. of Roentgenology*, 152:247-252 (Feb., 1989).

PARAMAGNETIC OIL EMULSIONS AS ENTERIC MRI CONTRAST AGENTS

BACKGROUND OF THE INVENTION

1. Field of the Invention

This invention relates to magnetic resonance imaging (MRI) of the human body and to the use of paramagnetic contrast agents to improve the diagnostic usefulness of the MR images. More particularly, this invention is concerned with paramagnetic oil emulsions as enteric MRI contrast agents and their use in MRI evaluation of the abdomen and pelvis.

2. Description of the Prior Art

Magnetic resonance imaging is a useful diagnostic tool due to its good tissue differentiation. The imaging is enhanced by use of paramagnetic contrast agents which affect the relaxation times T1 (spin-lattice) and T2 (spin-spin) of hydrogen atoms present in the body materials. In abdominal MRI, bowel loops and intraluminal contents can mimic pathology such as adenopathy, pancreatic or other retroperitoneal lesions. Therefore, the development of a reliable oral MRI contrast agent is required before gastrointestinal MRI can assume a major role clinically.

Current review articles indicate that a problem in gastrointestinal tract MRI examinations has been stimulation of peristalsis, lack of contrast, and the lack of acceptable oral contrast agents. Particularly, magnetic contrast agents have not been developed for small bowel lumen. Clanton, Jeffrey A., "Oral Contrast Agents," *Magnetic Resonance Imaging*, Vol. I, Chap. 48, pp. 830-837, W. B. Saunders Company (1988). Stark, David D. and Bradley, William G., Jr., "Gastrointestinal Contrast Agents," *Magnetic Resonance Imaging*, pp. 1134-1139, The C. V. Mosby Company, St. Louis, Mo. (1988).

In the past few years, a variety of agents have been advocated as potential oral MRI contrast agents. However, none of them satisfies all the criteria of a satisfactory agent including: uniform effect throughout the gastrointestinal tract; good patient acceptance; no side effects; and ability to mix freely with intestinal contents. The potential oral MRI contrast agents that have been proposed can be divided into four different categories.

The first group includes miscible positive agents, such as $MnCL_2$, Burnett, K. R., Goldstein, E. J., Wolf, G. L., Sen, S., and Mamourian, A. C., "The Oral Administration of $MnCl_2$: A Potential Alternative to IV Injection for Tissue Contrast Enhancement in Magnetic Resonance Imaging," *Magnetic Resonance Imaging*, Vol. 2, pp. 307-314, Pergamon Press, Ltd. (1984); Mamourian, A. C., Burnett, K. R., Goldstein, E. J., Wolf, G. L., Kressel, H. Y. and Baum, S., "Proton Relaxation Enhancement in Tissue Due to Ingested Manganese Chloride: Time Course and Dose Response in the Rat," *Physiological Chemistry and Physics and Medical NMR*, 16, pp. 123-128 (1984); dilute iron aqueous solutions such as Geritol®, ferric ammonium citrate, Wesbey, G. E., Brasch, R. C., Goldberg, H. I., and Engelstad, B. L., "Dilute Oral Iron Solutions as Gastrointestinal Contrast Agents for Magnetic Resonance Imaging; Initial Clinical Experience," *Magnetic Resonance Imaging*, Vol. 3, pp. 57-64 (1985); metal chelates, Runge, V. M., Stewart, R. G., Clanton, J. A., Jones, M. M., Lukehart, C. M., Partain, C. L., and James, A. E., Jr., "Work in Progress: Potential Oral and Intravenous Paramagnetic NMR Contrast Agents," *Radiology*, Vol. 147, No. 3, pp. 789-791 (June, 1983); and Gd-DTPA with mannitol, Laniado, M., Kornmesser, W., Hamm, B., Clauss, W., Weinmann, H. J., and Felix, R., "MR Imaging of the Gastrointestinal Tract: Value of Gd-DTPA," *Amer. Jour. of Roentgenology*, 150:817-821 (April, 1988). Oral contrast agents in aqueous solutions including osmotically active material, such as mannitol, are taught by U.S. Pat. No. 4,719,098. The disadvantages of these agents include significant dilutional effect from gastric, biliary and pancreatic secretions in the proximal small bowel resulting in failure to show effects distal to the ligament of Treitz, patient non-acceptance of metallic taste, complex absorptive process in the distal small bowel resulting in unpredictable and varying concentrations in the GI tract, and in the case of Gd-DTPA with mannitol some patients experienced diarrhea, probably due to the osmotic effect of mannitol.

The second group includes immiscible negative agents such as ferrite particles, Widder, D. J., Edelman, R. R., Grief, W. L. and Monda, L., "Magnetite Albumin Suspension: A Superparamagnetic Oral MR Contrast Agent," *Amer. Jour. of Roentgenology*, 149:839-843 (October, 1987); Hahn, P. F., Stark, D. D., Saini, S., Lewis, J. M., Wittenberg, J., and Ferrucci, J. T., "Ferrite Particles for Bowel Contrast in MR Imaging: Design Issues and Feasibility Studies," *Radiology*, 164, pp. 37-41 (July, 1987). Micellular particles such as phospholipid vesicles enclosing a paramagnetic material as contract agents for NMR imaging is taught by U.S. Pat. No. 4,728,575. These vesicles are targeted to accumulate in tumor tissue after intravenous injection. Aqueous suspensions of particles of water insoluble paramagnetic compounds suitable for oral or rectal administration for gastrointestinal NMR are taught by U.S. Pat. 4,615,879. Superparamagnetic metal oxides coated with polysaccharides are taught to be biologically degradable and a contrast agent for MRI by U.S. Pat. No. 4,827,945. The disadvantages of this group include the fact that with high concentrations, the homogeneity of the magnetic field may be distorted and produce image artifacts. This is especially detrimental in gradient echo imaging.

The third group includes immiscible positive agents such as aqueous oil emulsions, Li, K.C.P., Tart, R. P., Storm, B., Rolfes, R., Ang, P., and Ros, P. R., "MRI Oral Contrast Agents: Comparative Study of Five Potential Agents in Humans," Proceedings of the Eighth Annual Meeting of the Society of Magnetic Resonance in Medicine, Amsterdam, Aug. 18, 1989, p. 791. The major disadvantage of this group is that even with very concentrated oil emulsions, the enhancement effect is not adequate when T1 weighted pulse sequences are used.

The fourth group includes immiscible negative agents such as $CO_2$ gas tablets, Weinreb, J. C., Maravilla, K. R., Redman, H. C., and Nunnally, R., "Improved MR Imaging of the Upper Abdomen with Glucagon and Gas," *J. Comput. Assist.*, Tomogr. 8, pp. 835-838 (1984), perfluorocarbons, Mattrey, R. F., Hajek, P. C., Gylys-Morin, V. M., Baker, L. L., Martin, J., Long, D. C., and Long, D. M., "Perfluorochemicals as Gastrointestinal Contrast Agents for MR Imaging: Preliminary Studies in Rats and Humans, *Amer. Jour. of Roentgenology*, 148, pp. 1259-1263 (June, 1987); Mattrey, R. F., Perfluorooctylbromide: A New Contrast Agent for CT, Sonography, and MR Imaging," *Amer. Jour. of Roentgenology*. 152:247-252 (February, 1989), and kaolin-pectin, Li, K.C.P., Tart, R. P., Storm, B., Rolfes, R., Ang, P., and Ros, P. R., supra. This group has high potentials. However, CO$_2$ is limited to applications to the proximal GI tract. Perfluorocarbons are not FDA approved yet for clinical use and kaolin-pectin may cause severe constipation in the dosages suggested.

SUMMARY OF THE INVENTION

This invention relates to a paramagnetic oil emulsion for enteric administration wherein the emulsion comprises about 5 to about 30 volume percent oil, preferably about 15 to about 25 volume percent oil, and about 70 to about 95 volume percent, preferably about 75 to about 85 volume percent, aqueous based paramagnetic carrier having dissolved therein a magnetic resonance contrast effective and less than a toxic amount of at least one water-soluble paramagnetic agent. By the terminology "aqueous based or aqueous paramagnetic agent carrier" we mean to include any aqueous media in which the water-soluble paramagnetic agent may be dissolved and which forms with the oil an emulsion. The aqueous based paramagnetic carrier preferably includes nutritious materials such as milk and, for oral administration, includes flavor enhancers, such as ice cream or similar aqueous based materials to render the oil emulsion acceptable for human oral ingestion. Inclusion of an aqueous based carrier such as ice cream, in addition to flavor enhancement, provides emulsifiers for stabilization of the oil emulsion over long periods of time. One skilled in the art can readily ascertain the "magnetic resonance imaging contrast effective and less than a toxic amount" of water-soluble paramagnetic agent suitable for use with the paramagnetic oil emulsion of this invention, depending upon the specific paramagnetic agent used. Suitable amounts are those providing desired magnetic resonance contrast while not inflicting any toxic effects to the patient.

This invention includes a method of imaging a body cavity, such as abdomen and pelvis, of a patient by magnetic resonance after enteric administration to the patient of a magnetic resonance contrast medium as described above. Particularly, the invention includes a method for obtaining an in vivo magnetic resonance image of the abdomen and/or pelvis of a human subject by administering enterically to the subject an effective amount of a paramagnetic oil emulsion as described above and obtaining the magnetic resonance image after a time period sufficient to allow the paramagnetic oil emulsion to pass to the desired portion of the gastrointestinal tract. The paramagnetic oil emulsion is preferably administered orally or rectally and effective distribution through the small intestine or colon, respectively, occurs within about 30 to about 180 minutes post oral administration, and almost immediately post rectal administration. Even distribution of the paramagnetic oil emulsion occurs through the gastrointestinal tract increasing the magnetic resonance signal intensity difference between the gastrointestinal tract and other abdominal organs or pathologic tissues without loss of anatomical detail.

DESCRIPTION OF PREFERRED EMBODIMENTS

While the paramagnetic oil emulsion of this invention may be formulated using any physiologically compatible oil, we have found that emulsions, wherein the oil comprises predominantly over 50 and up to 100 volume percent vegetable oil, function satisfactorily. In preferred embodiments, the vegetable oil may be selected from corn, olive, peanut, soybean, and mixtures of such oils. Corn oil is a particularly preferred oil. We have found that for most commonly used magnetic resonance spin echo and gradient echo pulse sequences the intensity of the corn oil emulsions peaks at about 15 to about 25 volume percent corn oil. We have also observed that none of the unmixed components of the paramagnetic oil of this invention has a high signal intensity with all pulse sequences: SPIN ECHO 550/22, SPIN ECHO 2000/90, FLASH 40/18/10, FLASH 40/18/30, FLASH 40/18/50., FLASH 40/18/70, and FLASH 40/18/90.

The aqueous based paramagnetic carrier portion of the paramagnetic oil emulsion of this invention may comprise any physiologically compatible aqueous solution. It is preferred that the aqueous based paramagnetic carrier be nutritious and of desirable taste. In preferred embodiments, the aqueous based paramagnetic carrier comprises milk and a flavor enhancer, such as ice cream or like flavoring components. We have found that where the aqueous based paramagnetic carrier comprises about 20 to about 50 volume percent milk and about 20 to about 40 volume percent ice cream, based upon the total of the oil emulsion, the taste of the paramagnetic oil emulsion is very acceptable to human patients. Other similar flavor enhancers may be used. Ice cream is a particularly preferred flavor enhancer since it also contains emulsifiers which provide very long-time stability to the paramagnetic oil emulsion.

Suitable paramagnetic agents for use in this invention are water-soluble paramagnetic agents known to the art in a magnetic resonance contrast effective and less than a toxic amount. The magnetic resonance contrast effective and toxic amount of specific water-soluble paramagnetic agents will be known to those skilled in the art, and if not, can be ascertained by routine experimentation. In preferred embodiments, the paramagnetic agent comprises an iron-based material, a particularly preferred magnetic agent is ferric ammonium citrate. Many currently used well-known paramagnetic agents are suitable for use in this invention, such as ferric ammonium citrate, gadolinium-DTPA, chromium-DTPA, chromium-EDTA, manganese-DTPA, manganese-EDTA, manganese chloride, iron sulfate and mixtures thereof. We have found that the magnetic resonance signal intensity peaks with use of ferric ammonium citrate present in the form of Geritol ® at about 7.5 to about 12.5 volume percent Geritol ®, based upon the total paramagnetic oil emulsion.

The aqueous based paramagnetic carrier and/or the paramagnetic agent may be provided in dehydrated dry powder form and mixed with water for formulating the paramagnetic oil emulsion. The paramagnetic oil emulsions of this invention may be formulated by mixing the oil and aqueous based paramagnetic carrier with the water-soluble paramagnetic agent in a blender, such as a Waring blender, at high speed for about two to five minutes. The paramagnetic oil emulsions will be stable for a time period sufficient to allow administration and imaging of a body cavity of a patient by magnetic resonance after enteric administration. However, physiologically compatible emulsifiers, such as are well-known to the art, for example as included in ice cream, may be added to the mixture which is emulsified to provide long-term storage stability of the emulsion.

The paramagnetic oil emulsion according to this invention may be used for imaging a body cavity of a patient by magnetic resonance after enteric administration to the patient of a magnetic resonance contrast medium of the above described paramagnetic oil emulsion. In preferred embodiments in vivo magnetic resonance images of the gastrointestinal tract of a human subject may be obtained by administering orally to the subject an effective amount of a paramagnetic oil emulsion as described above followed by obtaining the magnetic resonance image after a time period sufficient to allow the paramagnetic oil emulsion to pass to the desired portion of the gastrointestinal tract. Methods of obtaining magnetic resonance images of gastrointestinal tracts are known to those skilled in the art and preferred methods are set forth in the following specific examples.

One preferred paramagnetic oil emulsion according to this invention has the formulation in volume percent: 38% milk, 30% ice cream, 20% corn oil, 12% Geritol ®. We have found this formulation provides a safe, effective MRI contrast agent with high patient acceptance for oral administration. We have found using this formulation that the entire small bowel becomes homogeneously brighter than surroundings when imaged with all commonly utilized magnetic resonance spin echo and gradient echo pulse sequences. We have found intensity enhancement to be much stronger using Gd-DTPA or ferric ammonium citrate based paramagnetic agents than when using ferrous sulfate.

The specific examples set forth embodiments of the invention in detail which are intended to be illustrative only and are not intended to limit the invention in any way.

EXAMPLE I

An aqueous/oil emulsion paramagnetic contrast agent according to one preferred embodiment of this invention was formulated by mixing the following components for 3 minutes in a blender at high speed to form 500 ml of the paramagnetic oil emulsion:

| Component | Volume Percent |
| --- | --- |
| Homogenized Milk | 38 |
| Melted ice cream (Breyer vanilla, 8% fat) | 30 |
| Corn oil (Mazola) | 20 |
| Geritol ® J. B. Williams Co. | 12 |

3.38 mg/ml $Fe^{+3}$ (ferric ammonium citrate)
0.16 mg/ml thiamine
0.16 mg/ml riboflavin
3.38 mg/ml niacinamide
0.13 mg/ml panthenol
0.03 mg/ml pyridoxine
1.69 mg/ml methionine
3.38 mg/ml choline bitartrate
Ethanol 12 volume percent Similar emulsions were formulated varying the amount of Geritol ® from 4 to 20 volume percent, the amounts of corn oil and ice cream being constant and the balance being milk.

EXAMPLE II

Emulsions prepared as described in Example I with varying Geritol ® content from 4 to 12 volume percent were taken orally by human volunteers in the amount of 500 ml uniformly over a two-hour period. The volunteers abstained food and drink for at least four hours prior to ingestion of the emulsions. The volunteers were asked to grade on a scale of 1 to 5: the taste of the emulsion (1 being great and 5 being intolerable), the amount of nausea experienced (1 being none and 5 being severe vomiting), and the amount of abdominal cramps (1 being none and 5 being severe). The volunteers also recorded the duration of discomfort, the timing and frequency of bowel movements and the overall impression of the emulsion ingestion. Results are shown in Table 1:

TABLE 1

| Geritol ® (% v/v) | Taste | Nausea | Abd. Cramps |
| --- | --- | --- | --- |
| 4 | 1 | 1 | 1 |
| 6 | 1 | 1 | 1 |
| 8 | 1 | 1 | 1 |
| 10 | 2 | 1 | 1 |
| 12 | 2 | 1 | 1 |

EXAMPLE III

The volunteers who ingested emulsions referred to in Example II were then imaged using either a 1.5 T Siemens Magnetom MR imager or a General Electric Signa MR imager. Spin echo (SE) pulse sequences with repetition time (TR) of 550 msec and echo time (TE) of 22 msec, and TR of 2000 msec and TE of 90 msec were used. Images were also obtained using gradient echo FLASH pulse sequences with TR of 50 msec, TE of 15 msec and flip angle of 40 degree pulse sequences. The images were then reviewed jointly by two radiologists to evaluate the ability of the contrast agent to opacify the gastrointestinal tract and to enhance delineation of the different abdominal organs. The delineation of the bowel organs were scored on a scale of 1 to 5, 1 being very poor and 5 being excellent, the results being tabulated in Table 2:

TABLE 2

| Geritol ® (% v/v) | % Small Bowel Opacified | Organ Delineation with Best Sequence | Degree of Bowel Enhancement | | |
| --- | --- | --- | --- | --- | --- |
| | | | SE 550/22 | SE 2000/90 | FLASH 50/15/40 |
| 4 | 20 | 2 | 1 | 4 | 3 |
| 6 | 50 | 3 | 2 | 4 | 3 |
| 8 | 70 | 4 | 3 | 4 | 4 |
| 10 | 80 | 4 | 4 | 5 | 5 |
| 12 | >90 | 5 | 5 | 5 | 5 |

EXAMPLE IV

The emulsion prepared as in Example I with 12 percent Geritol ® was taken in 500 ml dosage orally by five human volunteers in the same manner as described in Example II followed by MR imaging in the same manner as described in Example III. The results, using the same scoring system as in Examples II and III is tabulated in Table 3.

TABLE 3

| Volunteer | Taste | Nausea | Abd. Cramps | % Small Bowel Opacified | Organ Delin. with Best Sequence | Degree of Bowel Enhancement | | |
|---|---|---|---|---|---|---|---|---|
| | | | | | | SE 550/22 | SE 2000/90 | FLASH 50/15/40 |
| 1 | 2 | 1 | 1 | >90 | 5 | 5 | 5 | 5 |
| 2 | 2 | 1 | 1 | >90 | 5 | 5 | 5 | 5 |
| 3 | 1 | 1 | 1 | >90 | 5 | 5 | 5 | 5 |
| 4 | 1 | 1 | 1 | 80 | 4 | 5 | 5 | 5 |
| 5 | 2 | 1 | 1 | 80 | 4 | 5 | 5 | 5 |

EXAMPLE V

Paramagnetic agents with various water/oil emulsions were formulated without ice cream and milk for human tests. In each case using Gd-DTPA 1 ml of the indicated paramagnetic agent from a stock solution of 0.5 M concentration was used with 100 ml corn oil (20 volume percent) and 400 ml water. For the iron based contrast agent, the iron content in the 500 ml emulsion was 0.2 gms (7mM). In each composition, the ingestion, imaging and evaluation procedures were the same as set forth in Examples II and III. Each composition was ingested by one person. Results are shown in the following Table 4:

TABLE 4

| Paramagnetic Agent | Oil | Taste | Nausea | Abd. Cramps | % Small Bowel Opacified | Organ Delin. with Best Sequence | Degree of Bowel Enhancement | | |
|---|---|---|---|---|---|---|---|---|---|
| | | | | | | | SE 550/22 | SE 2000/90 | FLASH 50/15/40 |
| Ferric Ammonium Citrate | Corn | 3 | 1 | 1 | 80 | 5 | 4 | 5 | 5 |
| Gd-DTPA | Corn | 3 | 1 | 1 | >90 | 5 | 5 | 5 | 5 |
| Gd-DTPA | Peanut | 3 | 1 | 1 | >90 | 5 | 5 | 5 | 5 |
| Gd-DTPA | Soybean | 3 | 1 | 1 | 80 | 5 | 5 | 5 | 5 |
| Ferrous Sulfate | Corn | 4 | 1 | 1 | 80 | 4 | 3 | 5 | 3 |

The above table shows that without the ice cream and milk the generic combinations tasted fairly bad. However, their distribution throughout the bowel and degree of opacification are very good to excellent with the various combination of ferric ammonium citrate, Gd-DTPA and the various vegetable oils. Ferrous sulfate produced less enhancement effect as compared to the other two paramagnetic substances tested. Soybean oil emulsion appeared to have a less uniform distribution throughout the bowel. From this study, it is apparent that many different combinations of a paramagnetic agent and an oil can work very well as an enteric MRI contrast agent.

EXAMPLE VI

A paramagnetic oil emulsion was formulated by mixing 150 ml melted ice cream, 250 ml homogenized milk, 100 ml corn oil, and 1.21 grams ferric ammonium citrate in a blender at high speed for three minutes. This homogeneous emulsion was taken orally and the subject scanned within 2 hours by MRI as described in Example III. Good delineation of the entire small bowel and good discrimination of the various abdominal organs was observed. The paramagnetic oil emulsion had a more acceptable taste than those in which Geritol® was used as the source of ferric ammonium citrate.

EXAMPLE VII

A paramagnetic oil emulsion was prepared in the same manner as described in Example VI except that instead of ferric ammonium citrate as the paramagnetic species, 1 ml of 0.5 M aqueous solution of Gadolinium DTPA was used. The Gd-DTPA did not add a metallic taste. In a similar manner, chromium EDTA may be used at concentrations of 0.1 to 10 mM/liter.

EXAMPLE VIII (COMPARISON)

An emulsion was made with different amount of corn oil and ice cream indicated in Table 5 with the balance being homogenized milk. These were tasted by human volunteers with the noted effects rated in the same manner as described in Example II followed in indicated cases by MR imaging in the same manner as described in Example III.

TABLE 5

| Corn Oil (% v/v) | Ice Cream (% v/v) | Taste | Nausea | Abd. Cramps | % Small Bowel Opacified | Organ Delin. with Best Sequence | Degree of Bowel Enhancement | | |
|---|---|---|---|---|---|---|---|---|---|
| | | | | | | | SE 550/22 | SE 2000/90 | FLASH 50/15/40 |
| 15 | 0 | 3 | 1 | 1 | 60 | 3 | 1 | 4 | 3 |
| 20 | 0 | 3 | 1 | 1 | 70 | 3 | 2 | 4 | 3 |
| 25 | 0 | 4 | 1 | 1 | 70 | 4 | 2 | 4 | 3 |
| 10 | 10-30 | 1 | | | | | | | |
| 20 | 10-30 | 1 | | | | | | | |
| 30 | 10-30 | 2 | | | | | | | |
| 40 | 10-30 | 2 | | | | | | | |

Table 5 shows that the MRI enhancement effect of the oil emulsion, without the paramagnetic agent is inadequate, especially with the T1 weighted SE sequence. Further, Table 5 shows that the taste is unacceptable without the inclusion of ice cream.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

We claim:

1. A paramagnetic oil emulsion for enteric administration, said emulsion comprising: about 5 to about 30 volume percent liquid oil and about 70 to about 95 percent liquid aqueous paramagnetic agent carrier, said aqueous paramagnetic agent carrier having dissolved therein a magnetic resonance imaging contrast effective amount and less than a toxic amount of at least one water soluble paramagnetic agent.

2. A paramagnetic oil emulsion according to claim 1 wherein said oil comprises predominately vegetable oil.

3. A paramagnetic oil emulsion according to claim 1 wherein said oil is vegetable oil selected from the group consisting of corn, olive, peanut, soybean, and mixtures of such oils.

4. A paramagnetic oil emulsion according to claim 1 wherein said aqueous paramagnetic agent carrier comprises milk and ice cream.

5. A paramagnetic oil emulsion according to claim 1 wherein said aqueous paramagnetic agent carrier comprises about 20 to about 50 volume percent milk and about 20 to about 40 volume percent ice cream, based upon the total said oil emulsion.

6. A paramagnetic oil emulsion according to claim 1 wherein said emulsion comprises about 15 to about 25 volume percent said oil and about 75 to about 85 volume percent said aqueous paramagnetic agent carrier.

7. A paramagnetic oil emulsion according to claim 1 wherein said wherein oil comprises predominately vegetable oil and said aqueous paramagnetic agent carrier comprises milk and ice cream.

8. A paramagnetic oil emulsion according to claim 1 wherein said emulsion comprises about 15 to about 25 volume percent vegetable oil selected from the group consisting of corn, olive, peanut, soybean, and mixtures of such oils.

9. A paramagnetic oil emulsion according to claim 1 wherein said paramagnetic agent is ferric ammonium citrate; said ferric ammonium citrate being present in an amount of about 0.75 to about 1.25 grams per dosage to a human adult.

10. A paramagnetic oil emulsion according to claim 1 wherein said oil comprises predominately vegetable oil, said aqueous paramagnetic agent carrier comprises milk and ice cream, said paramagnetic agent is ferric ammonium citrate; said ferric ammonium citrate being present in an amount of about 0.75 to about 1.25 grams per dosage to a human adult and said aqueous paramagnetic agent carrier comprises about 20 to about 50 volume percent milk and about 20 to about 40 volume percent ice cream, based upon the total said oil emulsion.

11. A paramagnetic oil emulsion according to claim 1 wherein said oil comprises corn oil in an amount of about 15 to 25 volume percent, said aqueous paramagnetic agent carrier comprises about 20 to about 50 volume percent milk and about 20 to about 40 volume percent ice cream, based upon the total said oil emulsion.

12. A paramagnetic oil emulsion for human oral administration, said emulsion comprising: about 5 to about 30 volume percent liquid oil and about 70 to about 95 volume percent liquid aqueous paramagnetic agent carrier, said aqueous paramagnetic agent carrier comprises a flavor enhancement agent and said aqueous paramagnetic agent carrier having dissolved therein a magnetic resonance image contrast effective amount and less than a toxic amount of at least one water soluble paramagnetic agent.

13. A paramagnetic oil emulsion according to claim 12 wherein said oil comprises predominately vegetable oil.

14. A paramagnetic oil emulsion according to claim 12 wherein said oil is vegetable oil selected from the group consisting of corn, olive, peanut, soybean, and mixtures of such oils.

15. A paramagnetic oil emulsion according to claim 12 wherein said aqueous paramagnetic agent carrier comprises about 20 to about 50 volume percent milk and about 20 to about 40 volume percent ice cream, based upon the total said oil emulsion.

16. A paramagnetic oil emulsion according to claim 12 wherein said emulsion comprises about 15 to about 25 volume percent said oil and about 75 to about 85 volume percent said aqueous paramagnetic agent carrier.

17. In a method of imaging a body cavity of a patient by magnetic resonance after enteric administration to the patient of a magnetic resonance contrast medium, the improvement comprising: administering enterically a paramagnetic oil emulsion, said emulsion comprising: about 5 to about 30 volume percent liquid oil and about 70 to about 95 volume percent liquid aqueous paramagnetic agent carrier, said aqueous paramagnetic agent carrier having dissolved therein a magnetic resonance imaging contrast effective amount and less than a toxic amount of at least one water soluble paramagnetic agent.

18. In a method of imaging according to claim 17 wherein said oil comprises predominately vegetable oil.

19. In a method of imaging according to claim 17 wherein said oil is vegetable oil selected from the group consisting of corn, olive, peanut, soybean, and mixtures of such oils.

20. In a method of imaging according to claim 17 wherein said aqueous paramagnetic agent carrier comprises milk and ice cream.

21. In a method of imaging according to claim 17 wherein said aqueous paramagnetic agent carrier comprises about 20 to about 50 volume percent milk and about 20 to about 40 volume percent ice cream, based upon the total said oil emulsion.

22. In a method of imaging according to claim 17 wherein said emulsion comprises about 15 to about 25 volume percent said oil and about 75 to about 85 volume percent said aqueous paramagnetic agent carrier.

23. In a method of imaging according to claim 17 wherein said wherein oil comprises predominately vegetable oil and said aqueous paramagnetic agent carrier comprises milk and ice cream.

24. In a method of imaging according to claim 17 wherein said emulsion comprises about 15 to about 25 volume percent vegetable oil selected from the group consisting of corn, olive, peanut, soybean, and mixtures of such oils.

25. A paramagnetic oil emulsion according to claim 17 wherein said paramagnetic agent is ferric ammonium citrate; said ferric ammonium citrate being present in an amount of about 0.75 to about 1.25 grams per dosage to a human adult.

26. In a method of imaging according to claim 17 wherein said oil comprises predominately vegetable oil, said aqueous paramagnetic agent carrier comprises milk an dice cream, said paramagnetic agent is ferric ammonium citrate; said ferric ammonium citrate being present in an amount of about 0.75 to about 1.25 grams per dosage to a human adult, and said aqueous based paramagnetic carrier comprises about 20 to about 50 volume percent milk and about 20 to about 40 volume percent ice cream, based upon the total said oil emulsion.

27. In a method of imaging according to claim 17 wherein said oil comprises corn oil in an amount of about 15 to 25 volume percent, said aqueous paramagnetic agent carrier comprises about 20 to about 50 volume percent milk and about 20 to about 40 volume percent ice cream, based upon the total said oil emulsion.

28. A method for obtaining an in vivo magnetic resonance image of the gastrointestinal tract of a human subject comprising: administering enterically to said subject an effective amount of a paramagnetic oil emulsion comprising about 5 to about 30 volume percent liquid oil and about 70 to about 95 volume percent liquid aqueous paramagnetic agent carrier, said aqueous paramagnetic agent carrier comprising a flavor enhancement agent and having dissolved in said aqueous paramagnetic agent carrier a magnetic resonance image contrast effective amount and less than a toxic amount of at least one water soluble paramagnetic agent; and obtaining the magnetic resonance image after a time period sufficient to allow said paramagnetic oil emulsion to pass to the desired portion of the gastrointestinal tract.

29. A method for obtaining an in vivo magnetic resonance image according to claim 28 wherein said paramagnetic oil emulsion is administered orally and said aqueous paramagnetic agent carrier comprises a flavor enhancement agent.

30. A method for obtaining an in vivo magnetic resonance image according to claim 28 wherein said paramagnetic oil emulsion is administered rectally.

31. A method for obtaining an in vivo magnetic resonance image according to claim 28 wherein said aqueous paramagnetic agent carrier comprises about 20 to about 50 volume percent milk and about 20 to about 40 volume percent ice cream, based upon the total said oil emulsion.

32. A method for obtaining an in vivo magnetic resonance image according to claim 28 wherein said oil comprises predominately vegetable oil.

33. A method for obtaining an in vivo magnetic resonance image according to claim 28 wherein said oil is vegetable oil selected from the group consisting of corn, olive, peanut, soybean, and mixtures of such oils.

34. A method for obtaining an in vivo magnetic resonance image according to claim 28 wherein said emulsion comprises about 15 to about 25 volume percent said oil and about 75 to about 85 volume percent said aqueous paramagnetic agent carrier.

35. A method for obtaining an in vivo magnetic resonance image according to claim 28 wherein said paramagnetic agent comprises ferric ammonium citrate present in an amount of about 0.75 to about 1.25 grams per dosage to a human adult.

* * * * *